United States Patent [19]

Neirinckx et al.

[11] 4,288,424

[45] Sep. 8, 1981

[54] GENERATOR FOR IONIC GALLIUM-68 BASED ON COLUMN CHROMATOGRAPHY

[76] Inventors: Rudi D. Neirinckx, Medfield; Michael A. Davis, Westwood, both of Mass.

[73] Assignee: Massachusetts Institute of Technology, Cambridge, Mass.

[21] Appl. No.: 3,552

[22] Filed: Jan. 15, 1979

[51] Int. Cl.$^3$ .................. A61K 43/00; B65D 71/00
[52] U.S. Cl. ......................... 424/1; 250/432 PD; 422/61; 521/25
[58] Field of Search .................. 424/1; 252/301.1 R; 422/61; 250/432 PD

[56] References Cited
PUBLICATIONS

Hackh's Chemical Dictionary, 3rd Ed, Blakiston Co., Philadelphia, 1950, pp. 365–366.

*Primary Examiner*—Leland A. Sebastian
*Assistant Examiner*—Christine M. Nucker
*Attorney, Agent, or Firm*—Arthur A. Smith, Jr.; Paul J. Cook

[57] ABSTRACT

A physiologically acceptable solution of gallium-68 fluorides, having an activity of 0.1 to 50 millicuries per milliliter of solution is provided. The solution is obtained from a generator comprising germanium-68 hexafluoride bound to a column of an anion exchange resin which forms gallium-68 in situ by eluting the column with an acid solution to form a solution containing $^{68}$Ga-fluorides. The solution then is neutralized prior to administration.

5 Claims, No Drawings

GENERATOR FOR IONIC GALLIUM-68 BASED ON COLUMN CHROMATOGRAPHY

The Government has rights in this invention pursuant to Contract No. E(11-1)-4115 awarded by the Department of Energy.

BACKGROUND OF THE INVENTION

This invention relates to radiopharmaceutical compositions containing gallium-68 and to a generator for preparing free ionic gallium-68.

Radiochemistry presently is utilized in biological research and medical diagnosis. Certain radioactive preparations, when introduced into a biological system, will localize in specific organs, tissues or skeletal material. With radiation detecting devices such as a gamma camera or a high pressure, multiwire proportional camera, the target areas are visualized and the functioning of certain organs such as the heart, the kidney or the liver then can be monitored to diagnose a particular disease or structural defect in the biological system. Presently, the technique of tomographic reconstruction is used to obtain three-dimensional images of specific organs. These images are obtained either by utilizing an x-ray source or by administering a composition containing a photon-emitting isotope. The use of a positron-emitting isotope is preferred over the use of single photons because lower activities can be used. In addition, the use of single photons requires a collimator to obtain the desired images. The use of a positron-emitting isotope does not require the use of a collimator since they emit 2 gamma particles in directions 180° from each other rather than in random directions.

Presently, the preferred positron-emitting isotopes for use in radiopharmaceutical preparations are oxygen-15, carbon-11, nitrogen-13 and fluorine-18. Unfortunately, all of these positron-emitting isotopes have a short half-life of less than 2 hours. Because of these short half-lives, it is necessary to have an on-site cyclotron producing these isotopes. Since a cyclotron is an expensive apparatus, it would be desirable to provide a positron-emitting isotope that would be available without the need for an on-site cycloron and which can be safely adminsitered to humans.

It has been known that it would be desirable to obtain free gallium-68, a positron-emitting isotope, in order to provide three-dimensional images. However, prior to this invention, no practical means for obtaining gallium-68 has been available. Presently, gallium-68 is available bound with ethylenediamine tetraacetic acid (EDTA). The problem with this compound is that it is cumbersome to isolate gallium-68 from the EDTA complexant so that the gallium-68 can be bound to other molecules for diagnostic use.

SUMMARY OF THE INVENTION

This invention provides generators for a water-soluble ion containing gallium-68 and physiologically acceptable compositions containing gallium-68 which are useful in the diagnosis of a disease or a structual defect of a biological system, particularly in humans. The ion containing gallium-68 is recovered from a generator comprising germanium-68 hexafluoride bound to an anion exchange resing. The gallium-68 is eluted selectively with an aqueous solution of hydrofluoric acid.

DESCRIPTION OF SPECIFIC EMBODIMENTS

The method for obtaining germanium-68 is not critical to this invention and any conventional procedure can be utilized. For example, gallium metal is exposed to an incident proton beam in the manner described in Int. J. Appl. Radiat. Isol., Vol. 8, pp 90 to 94. High yields of the germanium-68 can be obtained which are sufficiently pure for subsequent use in forming gallium-68 solutions which can be administered to biological systems.

The purified germanium-68 solution is evaporated to dryness and then is fixed to an anion exchange column by first forming a solution comprising hydrogen fluoride at a normality of between about $10^{-3}$ and $10^{-2}$, preferably between about 0.005 and 0.01 normality. This solution is percolated through a preequilibrated anion exchange resin in order to load the germanium-68 hexafluoride onto the resin by anion exchange. When it is desired to elute the gallium-68 fluoride, the same acidic solution is used for elution from the resin and to separate it from the bound germanium-68 hexafluoride. The anion exchange resin utilized for this purpose is in a highly positive form which is formed from a highly positively charged resin such as that charged with quaternary ammonium salt groups, pyridinium salts or the like which is then ionized in an aqueous solution. Alternative suitable resins incorporate polyalkylamine groups or mixtures of quaternany and tertiary ammonium groups. The germanium-68 hexafluoride then replaces the hydroxyl groups or other anions of the resin. Since mesh size controls the speed of the equilibrium, it is preferred to utilize small size anion exchange resins having a mesh size of between about 200 and 400. The eluted gallium-68 flouride solution then is neutralized with a basic material such as phosphate buffer, sodium hydroxide, sodium hydroxide, sodium citrate or the like to form a physiologically acceptable composition. The resultant soluction of gallium-68 is physiologically acceptable, contains gallium-68 having an activity of between about 0.1 and 50 millicuries per milliliter of gallium-68 solution, preferably between about 3 and 10 millicuries, so that it can be administered to animals including humans such as by intraveneous administration.

Using gallium-68 as a tracer, the $K_D$ for gallium was determined to be less than 20 for equilibration between the 0.01N HF solution and the anion-exchange resin. On this basis, it appears that all the gallium should be eluted from the column.

A particularly suitable means for preparing a physiologically acceptable solution of this invention is to provide the elution compositin and a physiologically acceptable neutralizing composition in a kit for use in conjunction with the gallium-68 generator. For example, 1 to 3 ml of a solution comprising 0.005N to 0.01N hydrofluoric acid can be hermetically and aseptically sealed in a plastic container having a volume of about 2 to 4 ml. An additional plastic vial which is partially evacuated is provided for the neutralizing agent for the acid such that when the eluting agent containing the gallium-68 hexafluoride is recovered from the germanium-68 generator, the neutralizing agent will form a solution which is preferably substantially isotonic with mammalian body fluids, e.g. human blood. The gallium-68 hydrofluoric acid solution obtained from the germanium-68 generator is combined with the contents of the evacuated vial containing the neutralizing agent. This is effected conveniently by providing a needle at the bottom of the column which punctures the seal of the evacuated vial to allow the gallium-68 solution to pass into the vial. The resultant physiologically acceptable solution then can be administered to a patent, for example, by injection into the blood stream of the patient.

Conveniently, the vial containing the physiologically acceptable solution is provided with a plunger means and a means for attaching a hypodermic needle so that the vial functions as a hypodermic syringe, whereby, after preparation of the solution, the contents can be injected parenterally without being transferred to another container or syringe.

Radioactive measurements are made in the conventional manner for a period beginning after injection and lasting from about 1 minute to about 4 hours.

The following example illustrates the present invention and is not intended to limit the same.

EXAMPLE I

This example illustrates the preparation of a pharmaceutically acceptable solution of gallium-68 fluoride useful in diagnosis.

Germanium-68 is dissolved in 0.01N HF solution. A 200-400 mesh anion-exchange column, Bio-Rad AG1×8, 0.4 cm in diameter and with a height of 2 cm was equilibrated with 0.01N HF solution and the $^{68}$Ge-solution eluted through the column.

In order to test for the optimum yields of gallium-68, eluting solutions were used ranging from 0.0001N to 0.1N in hydrofluoric acid. All samples were counted on a NaI (Tl) well-type crystal and the half-life and purity of the eluted activity determined under each of the eluting conditions. High-resolution gamma-ray spectra of the eluted samples were obtained using a Ge(Li) detector.

In addition, the distribution constants ($K_D$) of germanium and gallium between the anion-exchange resin and the various HF solutions were investigated by batch equilibration. The $K_D$ was calculated from the expression:

$$\frac{\text{Activity/g resin}}{\text{Activity/g liquid phase}}$$

The radioactive tracers used in these studies were germanium-68 and gallium-68.

The behavior of the Ge-68 adsorbed on a 0.25 ml column eluted with the 0.01N HF was determined. Up to a volume of approximately 3,000 ml, the level of germanium breakthrough, expressed as a percentage of the germanium loaded on the column, lies below the detection limit imposed by the experimental conditions ($10^{-3}$%), and after 3,000 ml, it becomes appreciable (ca $10^{-2}$%). Table I shows the variation of Ge-68 breakthrough observed in one collection volume as a function of hydrofluoric acid normality.

TABLE I

| VARIATION OF Ge-68 BREAKTHROUGH WITH HYDROFLUORIC ACID CONCENTRATION | |
|---|---|
| $N_{HF}$ | % Ge-68 Breakthrough |
| 0 | $<10^{-3}$* |
| 0.1 | $<10^{-3}$ |
| 0.2 | $<10^{-3}$ |
| 0.3 | $<10^{-3}$ |
| 0.5 | $<10^{-3}$ |
| 1.0 | $<10^{-3}$ |

*% breakthrough = $\frac{\text{Ge-68 breakthrough/collection volume}}{\text{Ge-68 added to the column}} \times 100$.

We claim:

1. The process for obtaining a physiologically acceptable aqueous solution of gallium-68 which comprises binding $^{68}$GeF$_6$= to an anion-exchange resin from a hydrofluoric acid solution whereby gallium-68 fluorides are formed in situ from said $^{68}$GeF$_6$=, eluting said gallium-68 fluorides from said resin with an aqueous HF solution and neutralizing the aqueous HF solution containing gallium-68 fluorides.

2. A kit for the preparation of a physiologically acceptable solution of gallium-68 from a resin column containing bound germanium 68 which comprises a first container having a volume of about 2 to 4 ml in which is aseptically and hermetically sealed a 0.005N to 0.01N HF solution and a second container having a volume of about 4 to 10 ml and in which is sealed a neutralizing agent for said acidic solution.

3. The kit of claim 2 wherein the second container is partially evacuated.

4. The kit of claim 3 wherein the second container is provided with a hypodermic syringe.

5. A generator for gallium-68 fluorides which comprises a column of an anion-exchange resin containing $^{68}$GeF$_6$= bound to said resin.

* * * * *